United States Patent
Mailland et al.

(10) Patent No.: US 9,446,027 B2
(45) Date of Patent: Sep. 20, 2016

(54) USE OF PIDOTIMOD TO TREAT IRRITABLE BOWEL SYNDROME

(71) Applicant: POLICHEM SA, Luxembourg (LU)

(72) Inventors: Federico Mailland, Lugano (CH); Francesco Scarci, Como (IT); Maurizio Caserini, Como (IT)

(73) Assignee: POLICHEM SA, Luxembourg (LU)

( * ) Notice: Subject to any disclaimer, the term of this patent is extended or adjusted under 35 U.S.C. 154(b) by 0 days.

(21) Appl. No.: 14/781,755

(22) PCT Filed: Apr. 5, 2013

(86) PCT No.: PCT/EP2013/057205
§ 371 (c)(1),
(2) Date: Oct. 1, 2015

(87) PCT Pub. No.: WO2014/161594
PCT Pub. Date: Oct. 9, 2014

(65) Prior Publication Data
US 2016/0058740 A1    Mar. 3, 2016

(51) Int. Cl.
| | | |
|---|---|---|
| A61K 31/427 | (2006.01) | |
| A61K 45/06 | (2006.01) | |
| A61K 9/00 | (2006.01) | |
| A61K 47/10 | (2006.01) | |
| A61K 47/12 | (2006.01) | |
| A61K 47/18 | (2006.01) | |
| A61K 9/06 | (2006.01) | |
| A61K 9/08 | (2006.01) | |
| A61K 47/36 | (2006.01) | |
| A61K 9/16 | (2006.01) | |
| A61K 9/20 | (2006.01) | |

(52) U.S. Cl.
CPC ........... *A61K 31/427* (2013.01); *A61K 9/0031* (2013.01); *A61K 9/0095* (2013.01); *A61K 9/06* (2013.01); *A61K 9/08* (2013.01); *A61K 9/1623* (2013.01); *A61K 9/2054* (2013.01); *A61K 45/06* (2013.01); *A61K 47/10* (2013.01); *A61K 47/12* (2013.01); *A61K 47/18* (2013.01); *A61K 47/183* (2013.01); *A61K 47/36* (2013.01)

(58) Field of Classification Search
CPC ............................ A61K 31/427; A61K 45/06
USPC ......................................................... 548/201
See application file for complete search history.

(56) References Cited

U.S. PATENT DOCUMENTS

| | | |
|---|---|---|
| 6,228,396 B1 | 5/2001 | Watts |
| 2003/0236255 A1 | 12/2003 | Waer et al. |
| 2007/0032477 A1 | 2/2007 | Waer et al. |
| 2009/0142769 A1 | 6/2009 | Crow et al. |

FOREIGN PATENT DOCUMENTS

| | | |
|---|---|---|
| CN | 101623499 A | 1/2010 |
| EP | 0572942 B2 | 11/2000 |
| IT | 1231723 B | 12/1991 |
| WO | 2009004569 A1 | 1/2009 |

OTHER PUBLICATIONS

Danese S., et al., "Review article: the role of anti-TNF in the management of ulcerative colitis—past, present and future," AP&T, Alimentary Pharmacology and Therapeutics, May 2013, vol. 37(9), pp. 855-866.
Prantera, "Glucocorticosteroids in the treatment of inflammatory bowel disease and approaches to minimizing systemic activity," Therapeutic Advances in Gastroenterology, Mar. 2013, vol. 6(2), pp. 137-156.
PCT International Search Report dated Sep. 2, 2013 for Intl. App. No. PCT/EP2013/057205, from which the instant application is based, 3 pgs.
AJG, The American Journal of Gastroenterology, vol. 104, Supp. 1, Jan. 2009, 40 pgs.
Hungihn, A.P.S. et al., Irritable bowel syndrome in the United States: prevalence, symptom patterns and impact, Aliment Pharmacol Ther 2005: 21:, pp. 1365-1375.
Olden, K.W., "Targeted therapies for diarrhea-predominant irritable bowel syndrome," Clinical and Experimental Gastroenterology, 2012:5 pp. 69-100.
Rasquin-Weber, A., et al. "Childhood functional gastrointestinal disorders," Gut 1999;45 (Suppl II):, pp. 1160-1168.

*Primary Examiner* — Kristin Vajda
(74) *Attorney, Agent, or Firm* — Fredrikson & Byron, P.A.

(57) ABSTRACT

The present invention is directed to the use of pidotimod, or a physiologically acceptable salt thereof, to treat irritable bowel syndrome. For the treatment of the present invention, pidotimod, or a physiologically acceptable salt thereof, may be administered either by oral route or rectally.

29 Claims, No Drawings

USE OF PIDOTIMOD TO TREAT IRRITABLE BOWEL SYNDROME

RELATED APPLICATIONS

This application is a 35 U.S.C. 371 national stage filing from, and therefore claims priority to, International Application No. PCT/EP2013/057205, which was filed Apr. 5, 2013 and the teachings of which are incorporated herein by reference.

The present invention is directed to the use of pidotimod, or a physiologically acceptable salt thereof, to treat irritable bowel syndrome.

BACKGROUND OF THE INVENTION

Irritable bowel syndrome (IBS) is a condition that affects millions of patients in Western Countries, including up to 55 million Americans, mostly women. IBS is characterized by a number of gastrointestinal signs and symptoms, including diarrhea or constipation, as well as bloating, pain, gas, and the potential for related conditions such as fibromyalgia. IBS is often confused with ulcerative colitis, or just colitis, as IBS can have many things in common with IBD, including diarrhea and abdominal pain. IBS, however, is not an inflammatory condition like IBD, and does not cause bleeding in the intestine or symptoms such as fever and weight loss.

A recent community-based survey found a prevalence of IBS in the US of approximately 14.1% (Hungin A P, Chang L, Locke G R, Dennis E H, Barghout V. Irritable bowel syndrome in the United States: prevalence, symptom patterns and impact. Aliment Pharmacol Ther. 2005;21:1365-1375). More than 80% of the surveyed patients were 18-54 years of age, and 64% were women.

IBS diagnoses are now often classified according to three symptom patterns: diarrhea-predominant IBS (IBS-D), constipation-predominant IBS (IBS-C), and an alternating pattern of these two (IBS-A). The true prevalence of each IBS subtype is not established, but IBS-A and IBS-D are thought to be more common. The negative impact of IBS symptoms on daily functioning and quality of life can be substantial (Olden K. Targeted therapies for diarrhea-predominant irritable bowel syndrome. Clinical and Experimental Gastroenterology 2012:5 69-100). Nearly 90% of patients with IBS-D report experiencing abdominal pain, gas, and sudden urgency and, as symptom severity increases, in the same way increases the level of impairment in daily functioning and quality of life. Patients with severe IBS symptoms may experience quality of life impairments that are comparable with, or even greater than, those associated with diabetes or depression.

The American College of Gastroenterology Updated in 2009 the Recommendations for Irritable Bowel Syndrome (American College of Gastroenterology Task Force on Irritable Bowel Syndrome. An evidence-based position statement on the management of irritable bowel syndrome. Am J Gastroenterol. 2009;104 (1): S1-S35.), including dietary recommendations and the use of the following three classes of drugs: tricyclic antidepressants (TCAs), antibiotics (ie, rifaximin), and the 5-HT3 antagonist alosetron. More recently, the FDA approved for the treatment of IBS symptoms the new agent linaclotide, a guanylate cyclase-C (GC-C) agonist. The effect of GC-C is to stimulate secretion of chloride and bicarbonate into the intestinal lumen, resulting in increased intestinal fluid and accelerated transit. Linaclotide has been shown to both accelerate GI transit and reduce intestinal pain. Other products used in Europe and other countries are dietary fibers and/or probiotics.

Whichever the treatment, the effect is only on clinical symptoms and does not last very long. Moreover, long lasting treatments are limited by the strong toxicity. Thus, there is still an unsatisfied medical need in terms of efficacy and prevention of relapses.

Pidotimod, whose chemical name is (4R)-3-(5-oxo-L-prolyl)-1,3-thiazolidine-4-carboxylic acid, was disclosed for the first time in IT1231723. It is a synthetic dipeptide with immunological modulatory activity on both the adaptive and innate immune responses. This compound has been shown to induce dendritic cell maturation and up-regulate the expression of HLA-DR and co-stimulatory molecules CD83 and CD86, which are integral to communication with adaptive immunity cells. Pidotimod has also been shown to stimulate dendritic cells to release pro-inflammatory molecules such as MCP-1 and TNF-α cytokines, and to inhibit thymocyte apoptosis caused by a variety of apoptosis inducing molecules.

It has now been surprisingly found that pidotimod, besides being active on illnesses characterized by immune defects, may be of benefit in patients with irritable bowel syndrome, by attenuating the symptoms including diarrhea, intestinal pain and flatulence.

DESCRIPTION OF THE INVENTION

The object of the present invention is represented by the use of pidotimod, or a physiologically acceptable salt thereof, for use in the treatment of irritable bowel syndrome.

For the treatment of the present invention, pidotimod, or a physiologically acceptable salt thereof, may be administered either orally or rectally.

When administered orally, it may be in the form of solid or liquid formulations containing pidotimod or a physiologically acceptable salt thereof together with at least a pharmaceutically acceptable excipient and/or adjuvant; such formulations may be in the form of tablets, film-coated tablets, capsules, dragées, sachets, solutions or suspensions.

Such liquid formulations to be orally administered may have a w/w concentration in pidotimod from 0.5% to 20%, more preferably from 1% to 10%, most preferably from 2% to 8%. Such solid formulations to be orally administered may have a w/w concentration in pidotimod from 50% to 90%, more preferably from 65% to 80%, most preferably from 70% to 75%.

According to an embodiment of the invention, when administered orally, the amount of pidotimod or of a physiologically acceptable salt thereof, may vary from 10 to 1000 mg per single dose, more preferably from 50 to 800 mg per single dose.

Such solid, semi-solid or liquid formulations are particularly suitable to treat irritable bowel syndrome in all its manifestations, including IBS-D, IBS-C and IBS-A.

When rectally administered, pidotimod, or a physiologically acceptable salt thereof, may be in the form of semi-solid or liquid formulations containing pidotimod or a physiologically acceptable salt thereof, together with at least a pharmaceutically acceptable excipient and/or adjuvant; such formulations may be in the form of enema, suppositories, solutions, emulsions or suspensions.

Such semi-solid or liquid formulations to be rectally administered may have a w/w concentration in pidotimod from 0.1% to 20%, more preferably from 1% to 15%, most preferably from 5% to 10%. They are particularly suitable to treat irritable bowel syndrome by direct application over the intestinal mucosa.

Pharmaceutical compositions may be prepared according to conventional techniques, may contain pharmaceutically acceptable excipients, adjuvants and/or carriers, and may also contain, in combination, one or more active principles with complementary or, in any case, useful activity. The active agents which may be used in combination with pidotimod of the present invention include, but are not limited to, tricyclic antidepressants, antibiotics, 5-HT3 antagonists and/or guanylate cyclase-C agonists, dietary fibers, probiotics. Such active ingredients may be administered together with pidotimod (i.e. they may be for instance contained in the same composition as pidotimod) or they may be administered separately from or in temporal proximity with pidotimod.

Examples of tricyclic antidepressants include amitriptyline, clomipramine, imipramine, nortryptiline; examples of antibiotics include rifaximin, neomycin, kanamycin, gentamicin, amikacin, streptomycin, other aminoglycosides and in general antibiotics which are not absorbed by the intestinal tract; examples of 5-HT3 antagonists include alosetron; examples of guanylate cyclase-C agonists include linaclotide; examples of probiotics include *Bifidobacterium* spp. and *Lactobacillus* spp.

Examples of the compositions prepared according to the present invention include: tablets, film-coated tablets, capsules, dragées, suspension or solutions suitable for oral administration; enema, suppositories, solutions, emulsions, suspensions for rectal application.

The pharmaceutical compositions and the uses of the present invention will now be more fully described by the following examples. It should, however, be noted that such examples are given by way of illustration and not of limitation.

EXAMPLE 1

A rectal solution having the following w/w % composition was prepared:

| | |
|---|---|
| 1. Pidotimod | 10.00% |
| 2. Tris(hydroxymethyl)methylamine | 5.00% |
| 3. Disodium EDTA | 0.10% |
| 4. Propylene Glycol | 5.00% |
| 5. Lactic acid | 0.15% |
| 6. Hydroxypropyl Chitosan | 1.00% |
| 7. Purified water | q.s. to 100.00% |

Preparation

Solubilize components 1, 2, 3, 4, 5 in water. Add component 6 and mix until clear solution is obtained.

EXAMPLE 2

A rectal gel formulation having the following w/w % composition was prepared:

| | |
|---|---|
| 1. Purified water | q.s to 100.00% |
| 2. Pidotimod | 10.00% |
| 3. Tris(hydroxymethyl)methylamine | 5.00% |
| 4. Disodium Edta | 0.10% |
| 5. Propylenglycol | 5.00% |
| 6. 5-Ureidohydantoin | 0.30% |
| 7. Thickeners | 0.80% |

-continued

| | |
|---|---|
| 8. Hydroxypropyl Chitosan | 0.50% |
| 9. Preservatives | 0.33% |

Preparation

In the main vessel combine the components 1, 2, 3, 4, 5, 6, and 9. Mix until clear solution. Add thickeners homogenizing after each addition and until fully dispersed. Separately solubilize component 8 in part of water and add it in the main vessel while stirring. Mix until homogeneity.

EXAMPLE 3

A granulate for oral administration having the following w/w % composition was prepared:

| | |
|---|---|
| 1. Pidotimod | 26.67% |
| 2. Mannitol | 3.33% |
| 3. Binder and wetting agent | 0.90% |
| 4. Sweetener | 0.60% |
| 5. Flavour | 16.67% |
| 6. Sodium carbonate anhydrous | 5.67% |
| 7. Silicon dioxide | 0.33% |
| 8. Colouring agents | 0.04% |
| 9. Saccharose | q.s. to 100% |

Preparation

In a vessel dissolve the component 3 in a suitable quantity of water. Mix until clear solution. In another vessel mix the components 1 and 2. Spray the obtained solution onto mixed components until a homogeneous granulate is obtained. After drying, components from 4 to 9 are added to the obtained granulate. All components are mixed until an homogeneous mixture is obtained.

EXAMPLE 4

A solution for oral administration having the following w/w % composition was prepared:

| | |
|---|---|
| 1. Pidotimod | 5.10% |
| 2. Sodium chloride | 0.07% |
| 3. Sodium saccharin | 0.06% |
| 4. Chelating agents | 0.05% |
| 5. Trometamine | 2.50% |
| 6. Preservatives | 0.15% |
| 7. Sorbitol solution | 31.89% |
| 8. Flavouring agents | 0.30% |
| 9. Antioxydants | 0.07% |
| 10. Colouring agents | 0.01% |
| 11. Purified water | 59.80% |

Preparation: in a vessel dissolve the components 1 to 10 in a suitable quantity of purified water. Mix until a clear solution is obtained. Add the remaining quantity of water, mix until a homogeneous solution is obtained and filter.

EXAMPLE 5

A tablet for oral administration having the following w/w % composition was prepared:

| | |
|---|---|
| 1. Pidotimod | 72.70% |
| 2. Diluents | 17.65% |
| 3. Sodium Carboxymethyl cellulose crosslinked | 4.55% |

-continued

| 4. Binders | 4.00% |
|---|---|
| 5. Magnesium stearate | 1.10% |

In a vessel mix the components 1 and 2. In another vessel dissolve the component 4 in a suitable quantity of water. Mix until a clear solution is obtained. Spray the obtained solution onto mixed components 1 and 2 until a homogeneous granulate is obtained. After drying, components 3 and 5 are added to the obtained granulate and mixed until a homogeneous mixture is obtained. The mixture is then compressed by means of a tableting machine.

EXAMPLE 6

Nine patients with IBS aged 25 to 60 years (5 female) were enrolled in an open label pilot trial to receive twice a day the composition as per the Example 4. IBS was diagnosed according to Rome II criteria for the diagnosis of IBS (Rasquin-Weber A: Childhood functional gastrointestinal disorders, Gut 1999;45 (Suppl II): II60-II68). Rome II Criteria for the Diagnosis of IBS: at least 12 weeks, which need not be consecutive, in the preceding 12 months of abdominal discomfort or pain that has at least two of the following three features:
1. Relieved by defecation.
2. Onset associated with changes in stool frequency.
3. Onset associated with changes in stool form.

The overall IBS scores (IBS Symptoms, Pain severity, Pain frequency, Bloating, Bowel habit dissatisfaction, Life interference) and extracolonic IBS scores were assessed at 4, 8, and 12 weeks during treatment.

Pidotimod taken for 12 weeks significantly improved overall IBS score (315 to 175, P<0.05). The post-treatment overall extracolonic IBS score was significantly lower (240 to 90, P<0.001) when compared with baseline value.

CONCLUSIONS

The result of this study showed that Pidotimod administered twice daily for 12 weeks has beneficial role in IBS.

The invention claimed is:

1. A method of treating irritable bowel syndrome in a patient, comprising administering to the patient pidotimod or a physiologically acceptable salt thereof.

2. The method of claim 1 wherein the irritable bowel syndrome is in form of IBS-D, IBS-C or IBS-A.

3. The method of claim 1 wherein the patient is a human.

4. The method of claim 1 comprising orally administering to the patient pidotimod or the physiologically acceptable salt thereof.

5. The method of claim 4 comprising orally administering to the patient a solid formulation of pidotimod or the physiologically acceptable salt thereof or a liquid formulation of pidotimod or the physiologically acceptable salt thereof.

6. The method of claim 5 wherein the solid formulation of pidotimod or the physiologically acceptable salt thereof is selected from a tablet, a film-coated tablet, a capsule, a dragée or a sachet.

7. The method of claim 5 wherein the liquid formulation of pidotimod or the physiologically acceptable salt thereof is selected from a solution or a suspension.

8. The method of claim 5 wherein the solid formulation of pidotimod or the physiologically acceptable salt thereof is a solid formulation having a w/w concentration of pidotimod from 50% to 90%.

9. The method of claim 8 wherein the solid formulation of pidotimod or the physiologically acceptable salt thereof is a solid formulation having a w/w concentration of pidotimod from 65% to 80%.

10. The method of claim 9 wherein the solid formulation of pidotimod or the physiologically acceptable salt thereof is a solid formulation having a w/w concentration of pidotimod or the physiologically acceptable salt thereof of from 70% to 75%.

11. The method of claim 5 wherein the liquid formulation of pidotimod or the physiologically acceptable salt thereof is a liquid formulation having a w/w concentration of pidotimod or the physiologically acceptable salt thereof of from 0.5% to 20%.

12. The method of claim 11 wherein the liquid formulation of pidotimod or the physiologically acceptable salt thereof is a liquid formulation having a w/w concentration of pidotimod or the physiologically acceptable salt thereof of from 1% to 10%.

13. The method of claim 12 wherein the liquid formulation of pidotimod or the physiologically acceptable salt thereof is a liquid formulation having a w/w concentration of pidotimod or the physiologically acceptable salt thereof of from 2% to 8%.

14. The method of claim 5 wherein the solid formulation of pidotimod or the physiologically acceptable salt thereof or the liquid formulation of pidotimod or the physiologically acceptable salt thereof has a content of pidotimod or the physiologically acceptable salt thereof of from 10 mg to 1000 mg per single dose.

15. The method of claim 14 wherein the solid formulation of pidotimod or the physiologically acceptable salt thereof or the liquid formulation of pidotimod or the physiologically acceptable salt thereof has a content of pidotimod or the physiologically acceptable salt thereof of from 50 mg to 800 mg per single dose.

16. The method of claim 1 comprising rectally administering to the patient pidotimod or the physiologically acceptable salt thereof.

17. The method of claim 16 rectally administering to the patient a semi-solid formulation of pidotimod or the physiologically acceptable salt thereof or a liquid formulation of pidotimod or the physiologically acceptable salt thereof.

18. The method of claim 17 wherein the semi-solid formulation of pidotimod or the physiologically acceptable salt thereof is a semi-solid formulation selected from a suppository, a cream, a gel, an ointment or an emulsion.

19. The method of claim 17 wherein the liquid formulation of pidotimod or the physiologically acceptable salt thereof is a liquid formulation selected from a solution or a suspension.

20. The method of claim 17 wherein the semi-solid formulation of pidotimod or the physiologically acceptable salt thereof or the liquid formulation of pidotimod or the physiologically acceptable salt thereof has a w/w concentration of pidotimod or the physiologically acceptable salt thereof of from 0.1% to 20%.

21. The method of claim 20 wherein the semi-solid formulation of pidotimod or the physiologically acceptable salt thereof or the liquid formulation of pidotimod or the physiologically acceptable salt thereof has a w/w concentration of pidotimod or the physiologically acceptable salt thereof of from 1% to 15%.

22. The method of claim 21 wherein the semi-solid formulation of pidotimod or the physiologically acceptable salt thereof or the liquid formulation of pidotimod or the physiologically acceptable salt thereof has a w/w concentration of pidotimod or the physiologically acceptable salt thereof of from 5% to 10%.

23. The method of claim 1 comprising administering to the patient pidotimod or a physiologically acceptable salt thereof in combination with or in temporal proximity with at least one additional active principle.

24. The method of claim 23 wherein the at least one additional active principle is selected from a tricyclic antidepressant, an antibiotic, a 5-HT3 antagonist, a guanylate cyclase-C agonist, a dietary fiber or a probiotic.

25. The method of claim 24 wherein the tricyclic antidepressant is selected from amitriptyline, clomipramine, imipramine and nortryptiline.

26. The method of claim 24 wherein the antibiotic is selected from rifaximin, neomycin, kanamycin, gentamicin, amikacin, streptomycin, another aminoglycoside or an antibiotic that is not absorbed by an intestinal tract.

27. The method of claim 24 wherein the 5-HT3 antagonist is alosetron.

28. The method of claim 24 wherein the guanylate cyclase-C agonist is linaclotide.

29. The method of claim 24 wherein the probiotic is a probiotic from the group of *Bifidobacterium* spp. or a probiotic from the group of *Lactobacillus* spp.

* * * * *